(12) United States Patent
Poplett

(10) Patent No.: US 7,846,217 B2
(45) Date of Patent: Dec. 7, 2010

(54) METHOD FOR A PARTIALLY ETCHED CAPACITOR LAYER INCLUDING A CONNECTION MEMBER

(75) Inventor: James M. Poplett, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/380,172

(22) Filed: Feb. 24, 2009

(65) Prior Publication Data

US 2009/0158565 A1    Jun. 25, 2009

Related U.S. Application Data

(60) Division of application No. 11/379,284, filed on Apr. 19, 2006, now Pat. No. 7,532,456, which is a continuation of application No. 11/065,873, filed on Feb. 25, 2005, now Pat. No. 7,180,727.

(51) Int. Cl.
*H01G 9/00*       (2006.01)
(52) U.S. Cl. ........................................... 29/25.03
(58) Field of Classification Search ................. 29/25.03
See application file for complete search history.

(56) References Cited

U.S. PATENT DOCUMENTS

| | | |
|---|---|---|
| 3,150,301 A | 9/1964 | Schils et al. |
| 3,182,238 A | 5/1965 | Toder et al. |
| 3,686,535 A | 8/1972 | Piper |
| 3,803,457 A | 4/1974 | Yamamoto |
| 3,993,508 A | 11/1976 | Erlichman |
| 4,033,848 A | 7/1977 | Strempel et al. |
| 4,059,216 A | 11/1977 | Meyer |
| 4,086,148 A | 4/1978 | Badia |
| 4,113,921 A | 9/1978 | Goldstein et al. |
| 4,171,477 A | 10/1979 | Funari |

(Continued)

FOREIGN PATENT DOCUMENTS

GB           825900         12/1959

(Continued)

OTHER PUBLICATIONS

"U.S. Appl. No. 11/065,873, Notice of Allowance mailed Sep. 21, 2006", 4 pgs.

(Continued)

*Primary Examiner*—Alexander G Ghyka
*Assistant Examiner*—Seahvosh J Nikmanesh
(74) *Attorney, Agent, or Firm*—Schwegman, Lundberg & Woessner, P.A.

(57) ABSTRACT

The present subject matter includes a method that includes joining a first connection member to an unetched connection area, the unetched connection area located on a single major surface of a first planar anode, forming a capacitor stack by aligning the first planar anode with at least a second planar anode, the second planar anode including at least a second connection member, the first connection member and the second connection member for electrical connection of the first planar anode to the second planar anode, aligning the first connection member and the second connection member to define an anode connection surface and joining the first planar anode and the second planar anode.

20 Claims, 11 Drawing Sheets

U.S. PATENT DOCUMENTS

| | | |
|---|---|---|
| 4,232,099 A | 11/1980 | Sullivan |
| 4,247,883 A | 1/1981 | Thompson et al. |
| 4,267,565 A | 5/1981 | Puppolo et al. |
| 4,571,662 A | 2/1986 | Conquest et al. |
| 4,614,194 A | 9/1986 | Jones et al. |
| 4,659,636 A | 4/1987 | Suzuki et al. |
| 4,676,879 A | 6/1987 | Salvadori |
| 4,763,229 A | 8/1988 | Ohtuka et al. |
| 4,931,899 A | 6/1990 | Pruett |
| 4,970,626 A | 11/1990 | Kakinoki et al. |
| 5,041,942 A | 8/1991 | Carrico |
| 5,142,439 A | 8/1992 | Huggett et al. |
| 5,173,375 A | 12/1992 | Cretzmeyer et al. |
| 5,195,019 A | 3/1993 | Hertz |
| 5,279,029 A | 1/1994 | Burns |
| 5,333,095 A | 7/1994 | Stevenson et al. |
| 5,369,547 A | 11/1994 | Evans |
| 5,384,685 A | 1/1995 | Tong et al. |
| 5,422,200 A | 6/1995 | Hope et al. |
| 5,428,499 A | 6/1995 | Szerlip et al. |
| 5,439,760 A | 8/1995 | Howard et al. |
| 5,469,325 A | 11/1995 | Evans |
| 5,471,087 A | 11/1995 | Buerger, Jr. |
| 5,493,259 A | 2/1996 | Blalock et al. |
| 5,493,471 A | 2/1996 | Walther et al. |
| 5,522,851 A | 6/1996 | Fayram |
| 5,559,667 A | 9/1996 | Evans |
| 5,584,890 A | 12/1996 | MacFarlane et al. |
| 5,628,801 A | 5/1997 | MacFarlane et al. |
| 5,660,737 A | 8/1997 | Elias et al. |
| 5,716,729 A | 2/1998 | Sunderland et al. |
| 5,734,546 A | 3/1998 | Kuriyama et al. |
| 5,737,181 A | 4/1998 | Evans |
| 5,748,438 A | 5/1998 | Davis et al. |
| 5,754,394 A | 5/1998 | Evans et al. |
| 5,779,891 A | 7/1998 | Andelman |
| 5,790,368 A | 8/1998 | Naito et al. |
| 5,800,724 A | 9/1998 | Habeger et al. |
| 5,800,857 A | 9/1998 | Ahmad et al. |
| 5,801,917 A | 9/1998 | Elias |
| 5,808,857 A | 9/1998 | Stevens |
| 5,811,206 A | 9/1998 | Sunderland et al. |
| 5,814,082 A | 9/1998 | Fayram et al. |
| 5,821,033 A | 10/1998 | Cromack et al. |
| 5,855,995 A | 1/1999 | Haq et al. |
| 5,867,363 A | 2/1999 | Tsai et al. |
| 5,908,151 A | 6/1999 | Elias |
| 5,922,215 A | 7/1999 | Pless et al. |
| 5,926,362 A | 7/1999 | Muffoletto et al. |
| 5,930,109 A | 7/1999 | Fishler |
| 5,949,638 A | 9/1999 | Greenwood, Jr. et al. |
| 5,963,418 A | 10/1999 | Greenwood, Jr. et al. |
| 5,968,210 A | 10/1999 | Strange et al. |
| 5,973,906 A | 10/1999 | Stevenson et al. |
| 5,980,977 A | 11/1999 | Deng et al. |
| 5,982,609 A | 11/1999 | Evans |
| 5,983,472 A | 11/1999 | Fayram et al. |
| 6,004,692 A | 12/1999 | Muffoletto et al. |
| 6,009,348 A | 12/1999 | Rorvick et al. |
| 6,032,075 A | 2/2000 | Pignato et al. |
| 6,040,082 A | 3/2000 | Haas et al. |
| 6,042,624 A | 3/2000 | Breyen et al. |
| 6,094,339 A | 7/2000 | Evans |
| 6,094,788 A | 8/2000 | Farahmandi et al. |
| 6,099,600 A | 8/2000 | Yan et al. |
| 6,110,233 A | 8/2000 | O'Phelan et al. |
| 6,110,321 A | 8/2000 | Day et al. |
| 6,117,194 A | 9/2000 | Strange et al. |
| 6,118,651 A | 9/2000 | Mehrotra et al. |
| 6,118,652 A | 9/2000 | Casby et al. |
| 6,139,986 A | 10/2000 | Kurokawa et al. |
| 6,141,205 A | 10/2000 | Nutzman et al. |
| 6,157,531 A | 12/2000 | Breyen et al. |
| 6,162,264 A | 12/2000 | Miyazaki et al. |
| 6,191,931 B1 | 2/2001 | Paspa et al. |
| 6,212,063 B1 | 4/2001 | Johnson et al. |
| 6,225,778 B1 | 5/2001 | Hayama et al. |
| 6,249,423 B1 | 6/2001 | O'Phelan et al. |
| 6,275,371 B1 | 8/2001 | Yoshio et al. |
| 6,275,729 B1 | 8/2001 | O'Phelan et al. |
| 6,297,943 B1 | 10/2001 | Carson |
| 6,299,752 B1 | 10/2001 | Strange et al. |
| 6,321,114 B1 | 11/2001 | Nutzman et al. |
| 6,324,049 B1 | 11/2001 | Inagawa et al. |
| 6,326,587 B1 | 12/2001 | Cardineau et al. |
| 6,375,688 B1 | 4/2002 | Akami et al. |
| 6,380,577 B1 | 4/2002 | Cadwallader |
| 6,388,284 B2 | 5/2002 | Rhodes et al. |
| 6,388,866 B1 | 5/2002 | Rorvick et al. |
| 6,402,793 B1 | 6/2002 | Miltich et al. |
| 6,409,776 B1 | 6/2002 | Yan et al. |
| 6,413,283 B1 | 7/2002 | Day et al. |
| 6,421,226 B1 | 7/2002 | O'Phelan et al. |
| 6,426,864 B1 | 7/2002 | O'Phelan et al. |
| 6,442,015 B1 | 8/2002 | Niiori et al. |
| 6,445,948 B1 | 9/2002 | Somdahl et al. |
| 6,451,073 B1 | 9/2002 | Farahmandi et al. |
| 6,493,212 B1 | 12/2002 | Clarke et al. |
| 6,509,588 B1 | 1/2003 | O'Phelan et al. |
| 6,522,525 B1 | 2/2003 | O'Phelan et al. |
| 6,556,863 B1 | 4/2003 | O'Phelan et al. |
| 6,571,126 B1 | 5/2003 | O'Phelan et al. |
| 6,585,152 B2 | 7/2003 | Farahmandi et al. |
| 6,674,634 B2 | 1/2004 | O'Phelan et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,736,956 B1 | 5/2004 | Hemphill et al. |
| 6,763,265 B2 | 7/2004 | O'Phelan et al. |
| 6,795,729 B1 | 9/2004 | Breyen et al. |
| 6,833,987 B1 | 12/2004 | O'Phelan |
| 6,885,887 B2 | 4/2005 | O'Phelan et al. |
| 6,957,103 B2 | 10/2005 | Schmidt et al. |
| 6,985,351 B2 | 1/2006 | O'Phelan et al. |
| 6,999,304 B2 | 2/2006 | Schmidt et al. |
| 7,072,713 B2 | 7/2006 | O'Phelan et al. |
| 7,107,099 B1 | 9/2006 | O'Phelan et al. |
| 7,120,008 B2 | 10/2006 | Sherwood |
| 7,154,739 B2 | 12/2006 | O'Phelan |
| 7,157,671 B2 | 1/2007 | O'Phelan et al. |
| 7,177,692 B2 | 2/2007 | O'Phelan et al. |
| 7,180,727 B2 | 2/2007 | Poplett |
| 7,190,569 B2 | 3/2007 | O'Phelan et al. |
| 7,190,570 B2 | 3/2007 | Schmidt et al. |
| 7,221,556 B2 | 5/2007 | Schmidt et al. |
| 7,347,880 B2 | 3/2008 | O'Phelan et al. |
| 7,355,841 B1 | 4/2008 | Schmidt et al. |
| 7,365,960 B2 | 4/2008 | O'Phelan et al. |
| 7,419,873 B2 | 9/2008 | Doffing et al. |
| 7,456,077 B2 | 11/2008 | Sherwood et al. |
| 7,532,456 B2 | 5/2009 | Poplett |
| 7,564,677 B2 * | 7/2009 | Poplett ........................ 361/508 |
| 2003/0072124 A1 | 4/2003 | O'Phelan et al. |
| 2003/0077509 A1 | 4/2003 | Probst et al. |
| 2003/0165744 A1 | 9/2003 | Schubert et al. |
| 2003/0195568 A1 | 10/2003 | O'Phelan et al. |
| 2004/0019268 A1 | 1/2004 | Schmidt et al. |
| 2004/0039421 A1 | 2/2004 | O'Phelan et al. |
| 2004/0114311 A1 | 6/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |

| | | | |
|---|---|---|---|
| 2004/0174658 | A1 | 9/2004 | O'Phelan et al. |
| 2004/0215281 | A1 | 10/2004 | O'Phelan et al. |
| 2004/0220627 | A1 | 11/2004 | Crespi et al. |
| 2005/0010253 | A1 | 1/2005 | O'Phelan et al. |
| 2005/0017888 | A1 | 1/2005 | Sherwood et al. |
| 2005/0052825 | A1 | 3/2005 | O'Phelan |
| 2006/0009808 | A1 | 1/2006 | Schmidt et al. |
| 2006/0012942 | A1 | 1/2006 | Poplett |
| 2006/0107506 | A1 | 5/2006 | Doffing et al. |
| 2006/0152887 | A1 | 7/2006 | Schmidt et al. |
| 2006/0174463 | A1 | 8/2006 | O'Phelan et al. |
| 2006/0179626 | A1 | 8/2006 | Poplett |
| 2007/0118182 | A1 | 5/2007 | O'Phelan et al. |
| 2008/0030928 | A1 | 2/2008 | Schmidt et al. |
| 2008/0154319 | A1 | 6/2008 | O'Phelan et al. |
| 2009/0002922 | A1 | 1/2009 | Doffing et al. |

FOREIGN PATENT DOCUMENTS

| | | |
|---|---|---|
| GB | 2132019 | 6/1984 |
| JP | 52-004051 | 1/1977 |
| JP | 59-083772 | 5/1984 |
| JP | 05-074664 | 3/1993 |
| JP | 2002-231582 | 8/2002 |
| WO | WO-9854739 A1 | 12/1998 |
| WO | WO-9951302 A1 | 10/1999 |
| WO | WO-99/66985 A1 | 12/1999 |
| WO | WO-00/19470 A1 | 4/2000 |
| WO | WO-0237515 A2 | 5/2002 |
| WO | WO-2006002148 A1 | 1/2006 |

OTHER PUBLICATIONS

"U.S. Appl. No. 11/065,873, Notice of Allowance mailed Oct. 18, 2005", 7 pgs.

"U.S. Appl. No. 11/065,873, Supplemental Amendment filed Apr. 19, 2005", 6 pgs.

"U.S. Appl. No. 11/379,284, Notice of Allowance mailed Dec. 31, 2008", 7 pgs.

"U.S. Appl. No. 11/379,284, Non-Final Office Action mailed Jun. 11, 2008", 17 pgs.

"U.S. Appl. No. 11/379,284, Response filed Dec. 1, 2008 to Non Final Office Action mailed Jun. 11, 2008", 12 pgs.

"U.S. Appl. No. 11/379,284, Response filed Feb. 19, 2008 to Non-Final Office Action mailed Oct. 17, 2007", 13 pgs.

"U.S. Appl. No. 11/379,284, Non-Final Office Action mailed Oct. 17, 2007", 19 pgs.

"U.S. Appl. No. 11/379,284, Response filed Sep. 18, 2007 to Restriction Requirement mailed Aug. 24, 2007", 7 pgs.

"U.S. Appl. No. 11/379,284, Restriction Requirement mailed Aug. 24, 2007", 5 pgs.

Doffing, B., et al., "Method and Apparatus for Providing Flexible Partially Etched Capacitor Electrode Interconnect", U.S. Appl. No. 10/996,903, filed Nov. 24, 2004, 239 Pgs.

Morley, A. R., et al., "Electrolytic capacitors: their fabrication and the interpretation of their operations behaviour", *The Radio and Electronic Engineer*, vol. 43, No. 7, (Jul. 1973), 421-429.

Porter, Mark C., "Handbook of Industrial Membrane Technology", *Handbook of Industrial Membrane Technology, Noyes Publications*, (1990), 623 Pages.

Schmidt, Brian L., et al., "Configurations and Methods for Making Capacitor Connections", U.S. Appl. No. 09/706,576, filed Nov. 3, 2000, 26 pgs.

Schmidt, Brian L., et al., "Method for Interconnecting Anodes and Cathodes in a Flat Capacitor", U.S. Appl. No. 11/325,931, filed Jan. 5, 2006, 28 pgs.

* cited by examiner

METHOD FOR A PARTIALLY ETCHED CAPACITOR LAYER INCLUDING A CONNECTION MEMBER

CROSS REFERENCE TO RELATED APPLICATIONS

The present application is a divisional of U.S. patent application Ser. No. 11/379,284, filed Apr. 19, 2006, now issued as U.S. Pat. No. 7,532,456, which is a continuation of U.S. patent application Ser. No. 11/065,873, filed on Feb. 25, 2005, now issued as U.S. Pat. No. 7,180,727, the specification of each of which is incorporated herein by reference in its entirety.

The present application is related to the following commonly assigned U.S. patents which are incorporated by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004. Additionally, the present application is related to the following Provisional U.S. Patent Application which is assigned to the same assignee and is incorporated by reference in its entirety: "Method and Apparatus for High Voltage Aluminum Capacitor Design," Ser. No. 60/588,905, filed on Jul. 16, 2004.

TECHNICAL FIELD

This disclosure relates generally to capacitors, and more particularly, to a method and apparatus for a partially etched capacitor layer including a connection member.

BACKGROUND

There is an ever-increasing interest in making electronic devices physically smaller. Consequently, electrical components become more compact as technologies are improved. However, such advances in technology also bring about additional problems. One such problem involves interconnects between various components and interconnects within components.

Interconnects are especially problematic with devices incorporating multiple layers. One such component is the capacitor. Capacitors provide improved charge storage and energy density using multiple conductive layers and advanced dielectrics. As the layers become more complex and smaller in dimensions, problems arise with interconnections.

Thus, there is a need in the art for improved technologies for interconnects between layered devices. The systems used to interconnect the multiple layers should be readily adapted for manufacturing. The interconnects should form robust connections without damaging the multiple layers and without sacrificing substantial performance of the component.

SUMMARY

The above-mentioned problems and others not expressly discussed herein are addressed by the present subject matter and will be understood by reading and studying this specification.

One embodiment of the present subject matter includes an apparatus which includes a capacitor stack including a plurality of substantially planar electrodes, a first partially etched anode of the capacitor stack including a first substantially unetched portion, a second anode of the capacitor stack, a first connection member joined to the first substantially unetched portion and a second connection member joined to the second anode and the first connection member.

One embodiment of the present subject matter includes an apparatus which includes a first substantially planar capacitor electrode, a second substantially planar capacitor electrode in stacked alignment with the first substantially planar capacitor electrode, and joining means for joining the first substantially planar capacitor electrode to the second substantially planar capacitor electrode, wherein the first substantially planar capacitor electrode includes surface means for joining the first substantially planar capacitor electrode to the joining means.

One embodiment of the present subject matter includes a capacitor stack including a first substantially planar anode which includes a first substantially unetched portion, with a first connection member joined to the first substantially unetched portion, a second substantially planar anode connected to a second connection member, with the first connection member and the second connection member joined, the first substantially unetched portion produced by a process including depositing a curable resin mask onto an electrode, curing the curable resin mask to the electrode, etching the electrode, the cured mask restricting the etch, removing the cured mask from the electrode and anodizing the electrode.

One embodiment of the present subject matter includes a method, including attaching a first connection member to an unetched connection area, the unetched connection area located on a single major surface of a first planar anode, forming a capacitor stack by aligning the first planar anode with at least a second planar anode, the second planar anode including at least a second connection member, the first connection member and the second connection member for electrical connection of the first planar anode to the second planar anode, aligning the first connection member and the second connection member to define an anode connection surface and joining the first planar anode and the second planar anode.

Various optional configurations are possible within the present scope. Some optional embodiments within the present scope include welds formed by stake welding and welds formed by laser welding. An interconnection member can be welded to planar electrodes in some optional embodiments. Some optional embodiments organize planar electrodes into elements. Some optional embodiments align multiple planar electrodes before welding. Some optional embodiments include a capacitor adapted to provide from about 5.3 joules per cubic centimeter of capacitor stack volume to about 6.3 joules per cubic centimeter of capacitor stack volume. Some optional embodiments include a capacitor adapted to provide approximately 5.8 joules per cubic centimeter of capacitor stack volume. Other options are possible without departing from the scope of the present subject matter.

This Summary is an overview of some of the teachings of the present application and is not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

For example, the sheet includes a first major surface which is visible, and a second major surface substantially parallel to the first which is hidden. In varying embodiments, a first pattern of mask 9804 is applied to the first surface, and a second pattern of mask 9806 is applied to the second surface.

In varying embodiments, the first pattern of mask 9804 and the second pattern of mask 9806 are shaped differently. In one example, the first and second pattern have different shapes, and cover varying areas of the sheet. For example, pattern 9804 covers a first area of electrode shape 9802, and pattern 9806 covers a second area of electrode shape 9802, and the first area covered by pattern 9804 of electrode shape 9802 is larger than the second area covered by pattern 9806 of electrode shape 9802.

It should be noted that in varying embodiments, the shape of pattern 9804 and the shape of pattern 9806 are chosen to assist in manufacturing. For example, in varying embodiments, electrode shape 9802 is cut from a sheet of etched and anodized electrodes. When a single sheet is populated with multiple electrodes, in varying embodiments, the choice of shape for pattern 9804 and pattern 9806 can aid in associated manufacturing steps.

In varying embodiments, transition line 9808 is skew to transition line 9810. Varying examples increase the bending stress at the transition between etched foil and non-etched foil, and by positioning the transition line 9808 and 9810 in varying configurations, the bending stress of the electrode 9802 is more evenly distributed about the foil, which, in some embodiments, reduces instances of cracking and breaking FIGS. 9A-9F illustrate varying patterns of mask for application to a foil, according to various embodiments of the present subject matter. In varying embodiments, the mask can populate the pattern 9804 or the pattern 9806 illustrated in FIG. 8. It should be noted that the line 9902 described in varying examples is equivalent to the line 9808 of pattern 9804, and line 9810 of pattern 9806.

Figure 9A:
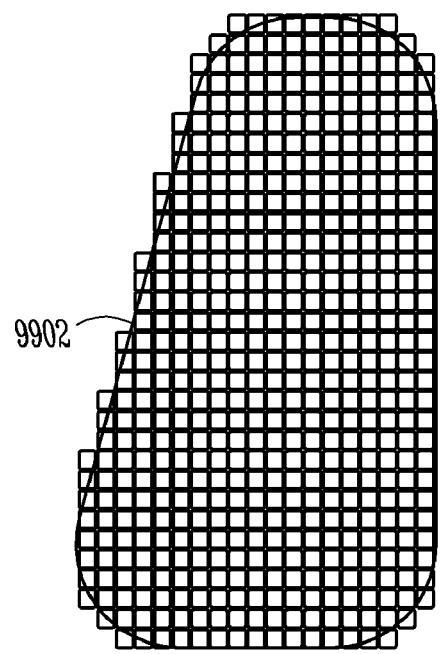

FIG. 9A illustrates an example of a mask constructed out of a pattern of rounded square shapes arranged proximal to each other. In varying embodiments, the shapes cover approximately 80% of the surface onto which they are printed, proximal the line 9902. Line 9902 defines, and the area proximal the line, define a transition zone between masked electrode and non-masked electrode. By angling the line 9902 in relation to other lines which define the mask, the pattern includes a varied interface at line 9902. The pattern at line 9902 resembles a set of steps.

Through the angle at line 9902, the pattern reduce instances of electrode breakage proximal to the transition zone. For example, in some embodiments, the electrode is etched and exhibits undercutting at the border between a masked portion and a non-masked portion. Parallel to this border is an axis which approximately bisects the undercut. Undercutting, in varying embodiments, results in a portion of the electrode which is weak while bending along the axis which bisects the length of the undercut. However, in varying embodiments, the undercut portion of the electrode is strong when bending orthogonal to an axis bisecting the length of the undercut. Thus, undercutting increases bending stress more in certain directions. By arranging the masking patter in the manner illustrated, the undercut portions of the electrode can be controlled to improve the flexibility of the electrode which reduces instances of breaking or cracking.

Figure 9B:
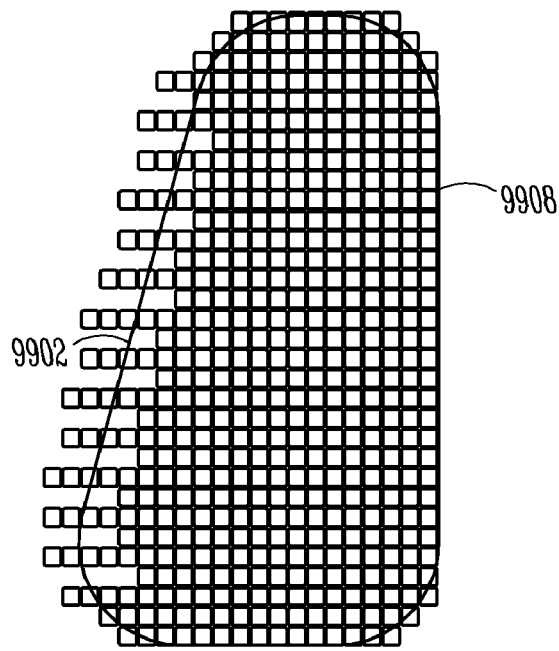

FIG. 9B illustrates an example of a mask constructed out of a pattern of rounded squares arranged proximal to each other. In varying embodiments, line 9902 defines an area across which elongate shapes span. It is apparent upon reading and understanding these teachings that the elongate shapes can be constructed out of rounded blocks, and that the elongate shapes can be defined in other fashions.

In varying embodiments, the mask includes exposed area 9908. In one example, exposed area 9908 is sized such that undercutting at the exposed area 9908 during etch does not substantially weaken the electrode under bending stress.

Figure 9C:
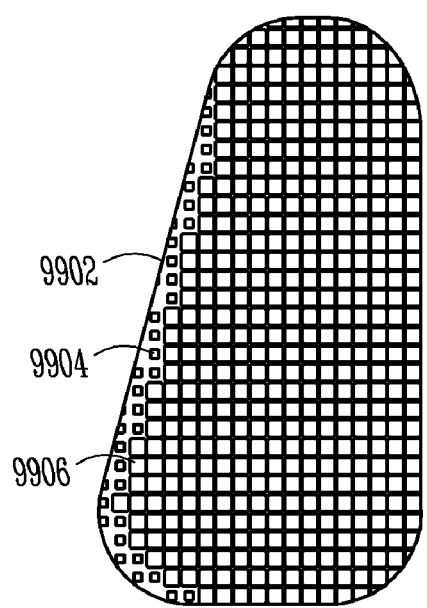

FIG. 9C illustrates one example of a halftone suitable for strengthening an electrode at the juncture between a masked portion and an unmasked portion. In one embodiment, the half tone is comprised for smaller rounded blocks 9904, and larger rounded blocks 9906. In one embodiment, the reach of the halftone is defined by a line 9902, and is limits to a transition zone proximal to the line 9902. In additional embodiments, the halftone is not defined as such.

In varying embodiments, the halftone transitions from covering approximately 80% of the electrode at the masked transition zone, to covering approximately 60% of the electrode at the masked transition zone. In varying embodiments, this can be accomplished with rounded blocks placed proximal to each other, and in additional embodiments, it is accomplished with other shapes arranged in a predictable pattern, such as a grid, or in a random pattern.

Figure 9D:
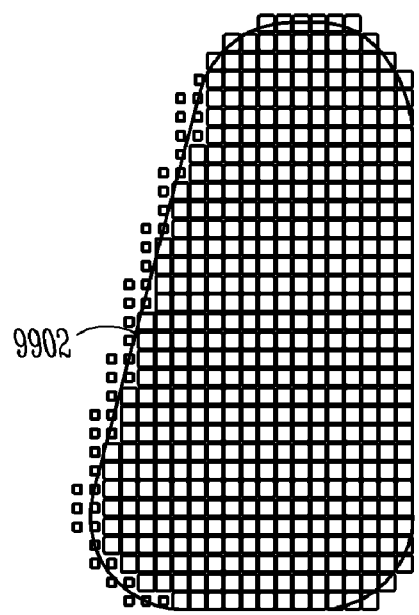

FIG. 9D illustrates an example of a halftone suitable for strengthening an electrode at the junction between a masked portion and an unmasked portion.

Figure 9E:
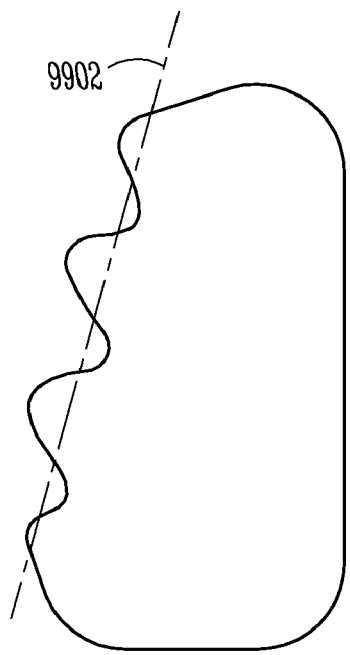

FIG. 9E illustrates an example of a pattern useful for strengthening an electrode in the region of a transition from a masked area to an unmasked area, according to various embodiments of the present subject matter. By including a sinusoidal shape which spans the line 9902, the instances of undercutting which are parallel to the bending line (the bending line is approximately parallel to transition line 9902) are minimized.

Figure 9F:
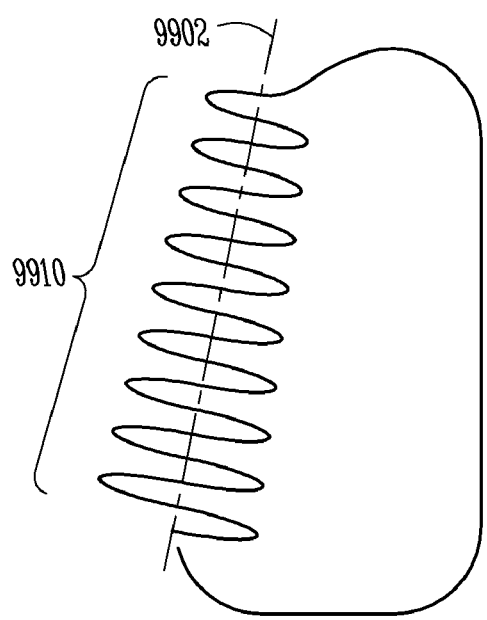

FIG. 9F illustrates a pattern for strengthening an electrode in an area where undercutting is put in bending stress, according to various embodiments of the present subject matter. In varying embodiments, the pattern is comprised of elongate shapes 9910. In varying embodiments, the elongate shapes demonstrate an improved resistance to cracking and breaking when the etched foil is subjected to bending stresses which are proximal the transition line 9902.

Figure 10:
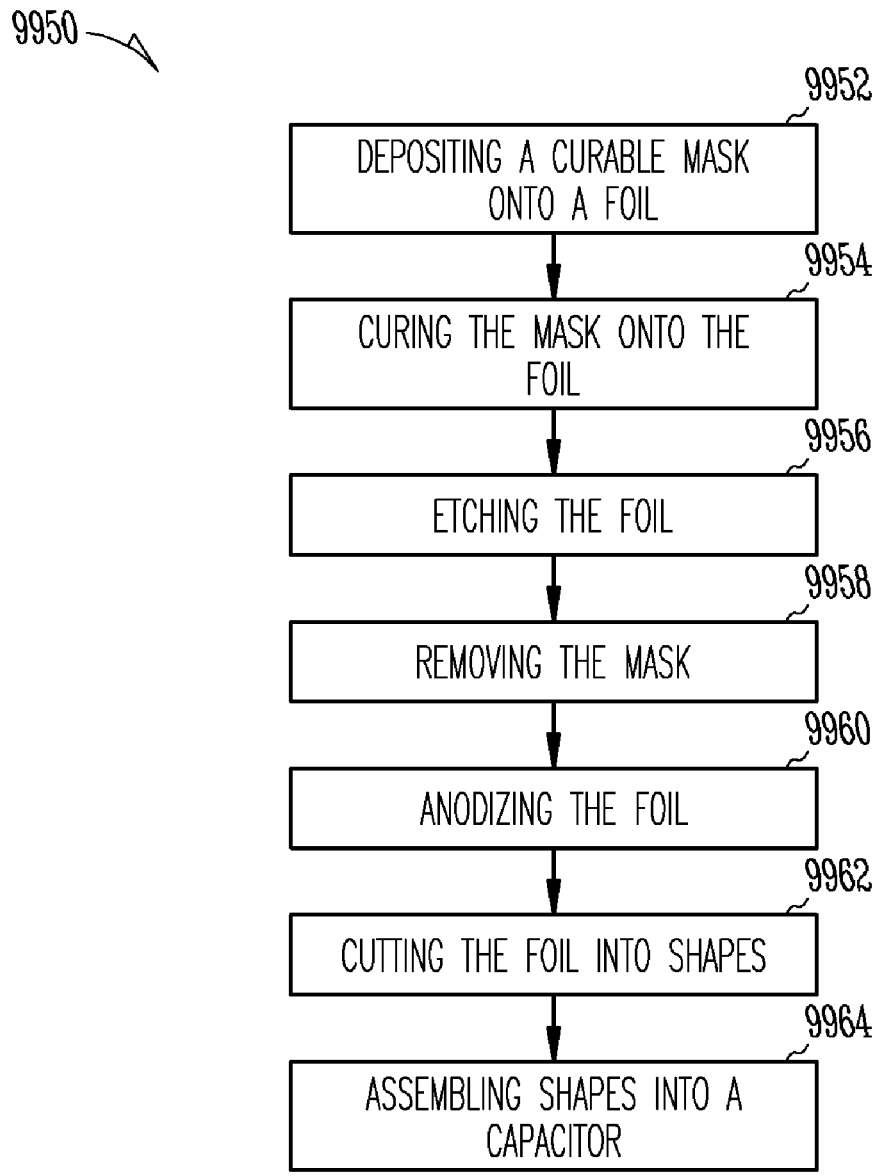

FIG. 10 shows a process for producing a foil 9950 with a partially etched area, according to various embodiments of the present subject matter. In varying examples, the process includes depositing a curable mask onto a foil 9952. For example, in one embodiment, the mask is deposited on a foil using a computer controlled mask dispensing system. In one example, ink is deposited using an ink jet process.

The control systems shown and described here can be implemented using software, hardware, and combinations of software and hardware. As such, the term "system" is intended to encompass software implementations, hardware implementations, and software and hardware implementations.

In various embodiments, the methods provided above are implemented as a computer data signal embodied in a carrier wave or propagated signal, that represents a sequence of instructions which, when executed by a processor, cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Additional embodiments cure the mask onto the foil 9954. Examples of curable mask include ink, and photoresist. In varying embodiments, the curable mask is cured to the foil. For example, in one embodiment, ink is deposited on the foil, and then is baked to the foil in an oven. Baking, in some embodiments, exposes the curable mask to radiant heat energy, which can increase hardness or the curable mask, and which also can decrease the time needed for curing. In varying embodiments, the oven is adapted to cure the curable mask without affecting the foil otherwise.

In varying embodiments, the foil is etched 9956, and the mask protects the foil from the etchant. Etching, in varying embodiments, is described in the discussion associated with FIG. 10, but in other embodiments, variations of the etching process are used.

Varying examples of the process then remove the mask 9958. Removing the mask, in one embodiment, includes submerging the foil with mask in a solution adapted to dissolve the mask.

Some embodiments anodize the foil 9960. Anodization, in one embodiment, is accomplished by the process discussed in the teachings associated with FIG. 10. However, these teachings should not be understood to be exhaustive or exclusive, and other methods of forming a dielectric on a foil are within the scope of the present subject matter. Additionally, it should be noted that other examples anodize the foil while the mask is in place.

Varying embodiments cut the anodized foil into shapes 9962, and in some examples, the foil shapes are then assembled into a capacitor 9964.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references may contemplate more than one embodiment. The following detailed description is, therefore, not to be taken in a limiting sense, and the scope is defined only by the appended claims, along with the full scope of legal equivalents to which such claims are entitled.

Figure 1:
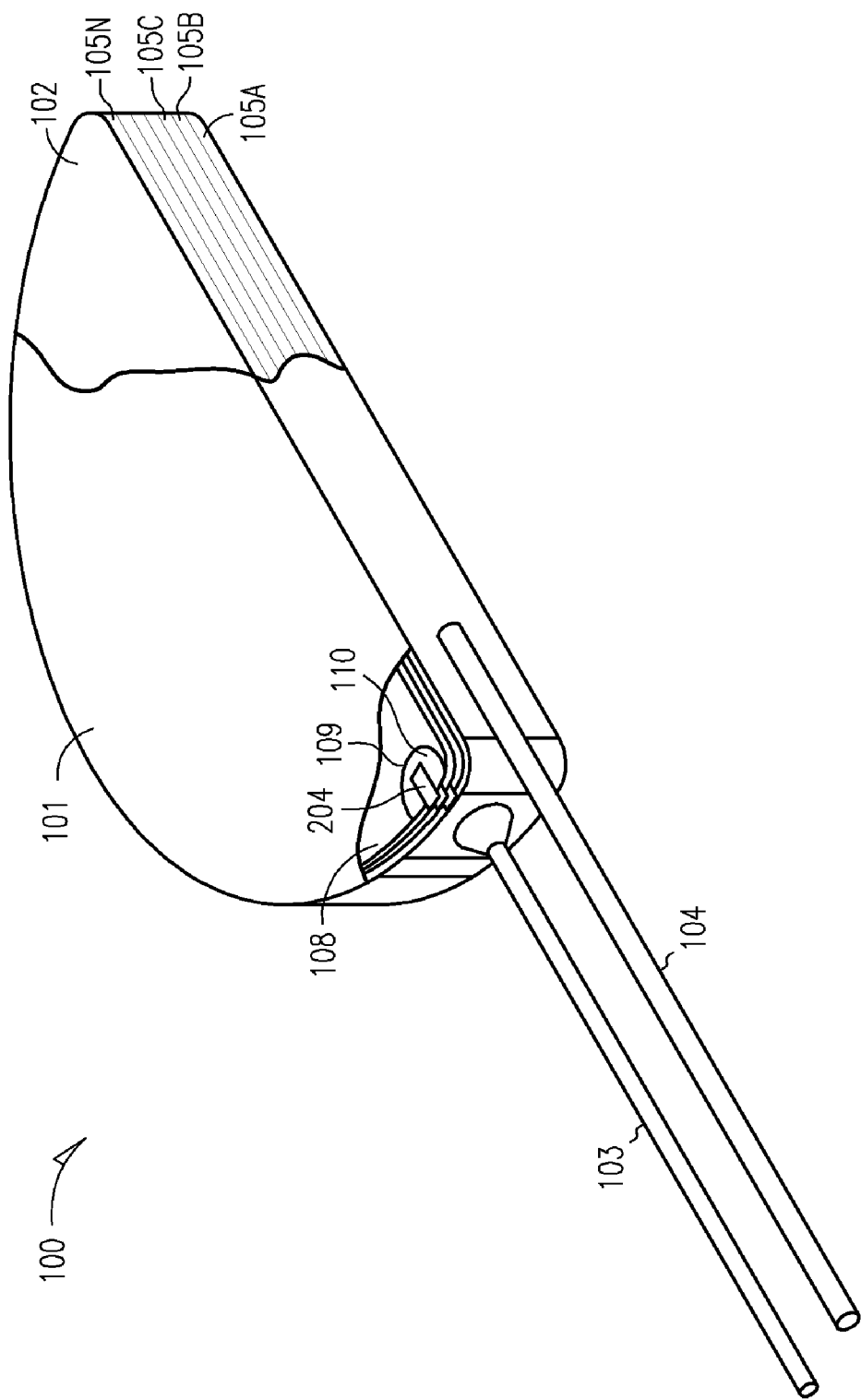
FIG. 1 is a perspective view of a capacitor according to one embodiment of the present subject matter.

FIG. 1 shows a flat capacitor 100 constructed according to one embodiment of the present subject matter. Although capacitor 100 is a D-shaped capacitor, in various embodiments, the capacitor is another desirable shape, including, but not limited to rectangular, circular, oval or other symmetrical or asymmetrical shape. Capacitor 100 includes a case 101 which contains a capacitor stack 102. In one embodiment, case 101 is manufactured from a conductive material, such as aluminum. In additional embodiments, the case is manufactured using a nonconductive material, such as a ceramic or a plastic.

In various embodiments, capacitor 100 includes a first terminal 103 and a second terminal 104 for connecting capacitor stack 102 to an outside electrical component, such as heart monitor circuitry, including defibrillator, cardioverter, and pacemaker circuitry. In one embodiment, terminal 103 is a feedthrough terminal insulated from case 101, while terminal 104 is directly connected to case 101. In various embodiments, the capacitor incorporates additional connection structures and methods. Additional connection structures and methods, such as embodiments including two or more feedthrough terminals as described on or around pages 12-13, 59-60, 63-82 of Provisional U.S. Patent Application, "Method and Apparatus for High Voltage Aluminum Capacitor Design," Ser. No. 60/588,905, filed on Jul. 16, 2004, are incorporated herein by reference, but not by way of limitation.

Capacitor stack 102 includes, in various embodiments, capacitor elements 105A, 105B, 105C, . . . , 105N, with each capacitor element 105A-105N including one or more cathodes, anodes, and separators. In various embodiments, each cathode is a foil structure and/or case include aluminum, tantalum, hafnium, niobium, titanium, zirconium, and combinations of these metals. In some embodiments, each cathode of capacitor stack 102 is connected to the other cathodes by welding or other connection methods. Additionally, in some embodiments, the cathodes are coupled to conductive case 101, and terminal 104 is attached to case 101 to provide a cathode connection to outside circuitry. In one embodiment, the cathode is coupled to a feedthrough conductor extending through a feedthrough hole.

Pictured in the example is an anode with an etched section 108, the anode having an unetched portion 110. Etching is discussed in various degrees throughout this application. Generally, etching as used herein relates to using chemicals to remove material. One specific form of etching which applies in various embodiments of the present subject matter involves roughening the surface of an electrode before growing a dielectric on the electrode. Following, in some embodiments, a dielectric coating is substantially absent from the unetched portion 110, and in additional embodiments a dielectric coating is present at unetched portion 110.

In various embodiments, the etch gradient is structured to reduce bending stress at the etch gradient 109. Etch gradient structure are described on or around pages 32-34, 115-119 of Provisional U.S. Patent Application Ser. No. 60/588,905. The teachings of those pages are incorporated herein by reference, but not by way of limitation.

A separator is located between each anode and cathode, in various embodiments. In one embodiment, the separator includes one or more sheets of kraft paper impregnated with an electrolyte. In one embodiment, the separator includes two sheets of paper. The electrolyte can be any suitable electrolyte for an electrolytic capacitor, such as an ethylene-glycol base combined with polyphosphates, ammonium pentaborate, and/or an adipic acid solute.

In one embodiment, one or more of the anodes of capacitor stack 102 are configured into an element which includes three foil layers. In various embodiments, an element include one, two, three or more anode foils having a variety of anode shapes. In various embodiments, anodes are generally foil structures and can include aluminum, tantalum, hafnium, niobium, titanium, zirconium, and combinations of these metals. In one embodiment, at least portions of a major surface of each anode foil is roughened and/or etched to increase its effective surface area. An etch may be measured using a surface roughness measurement, for example. Roughness imparted on the surface increases the capacitive effect of the foil with no relative increase in volume. Various embodiments incorporate other foil compositions and/or classes of foil compositions.

In various embodiments, the present subject matter includes anodes which have unetched portions on a single side of an anode layer. In some embodiments, these single-sided portions are substantially constrained to a single approximately planar face of an anode. Additionally, single sided portions in some embodiments are primarily constrained to a first approximately planar face of an anode, with sections of the unetched portion extending to second approximately planar face of the anode. In one embodiment, each anode is connected to the other anodes of the capacitor and is coupled to feedthrough assembly 103 for electrically connecting the anode to circuitry outside the case. In some embodiments, the anodes are connected to the case and the cathodes are coupled to a feedthrough assembly. In various embodiments, both the anode and the cathode are connected to components through feedthroughs.

Various embodiments include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

Attached to anode stack 102 is a connection structure such as a tab or connection member 204. In various embodiments, the connection member 204 is made from aluminum, which electrically connects each anode foil to the other anodes of the capacitor. In various embodiments, multiple anodes include multiple connected connection members. For instance, in the present embodiment, each connection member 204 of each capacitor element 105A, . . . , 105N is connected to each another connection member 204 and coupled to terminal 103 for electrically coupling the anode to a component or electronic assembly outside the case 101.

Figure 2:
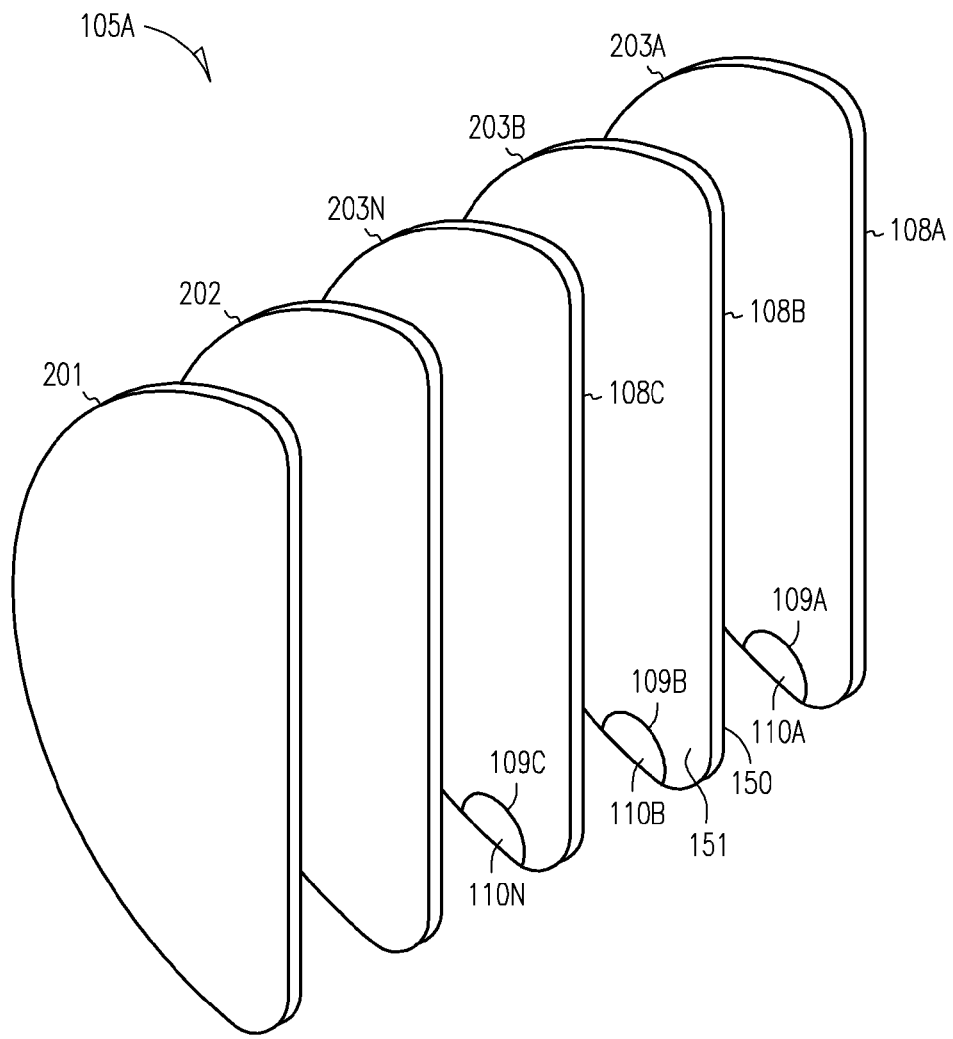
FIG. 2 is an exploded perspective view of a capacitor element, according to one embodiment of the present subject matter.

FIG. 2 shows details of one example of capacitor element 105*a*, which is representative of capacitor elements 105B-105N illustrated in the example FIG. 1. Element 105A includes a cathode 201, a separator 202, and an anode stack including anode layers 203A, 203B, . . . , 203N. In various embodiments, other numbers and arrangements of anodes, cathodes, and separators are utilized. Related Provisional U.S. Patent Application "Method and Apparatus for High Voltage Aluminum Capacitor Design," Ser. No. 60/588,905, filed on Jul. 16, 2004 discusses additional methods on or around pages 13-29 which are incorporated here by reference, but not by way of limitation.

For explanation, number flags of the present illustration match the example illustrated in FIG. 1, but this relationship should not be interpreted as limiting. Cathode 201 is a foil attached to other cathodes of capacitor stack 102 and to terminal 104 of the example FIG. 1. In some embodiments, cathode 201 can include aluminum, tantalum, hafnium, niobium, titanium, zirconium, and combinations of these metals. In one embodiment, cathode 201 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in $TiO$, $TiO_2$, $TiN$, $Ti_2O_5$, or other high dielectric constant oxide.

Titanium-coated cathode material has a higher capacitance per unit area than traditional aluminum electrolytic capacitor cathodes, in various embodiments. Some cathodes which are 98% aluminum purity or higher generally have capacitance per unit area of approximately 250 $uF/cm^2$ for 30 micron thick foil, with an oxide breakdown voltage in the 1-3 volt range. However, a cathode as described herein results in a capacitance per unit area which, in some embodiments, is as high as 1000 $uF/cm^2$ or more.

Advantageously, this provides a single cathode which services several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen gas as a byproduct which in turn has the effect of creating an internal pressure within the capacitor causing an undesirable mechanical bulge in the layers from the capacitor stack, or in the case. Therefore, the titanium-coated cathode described above serves as a corrective mechanism for hydrogen generation.

Separator 202 is located between each anode stack 203A, 203B, . . . , 203N and cathode 201. In one embodiment, separator 202 consists of two sheets of 0.0005 inches thick kraft paper impregnated with an electrolyte. In some embodiments, separator 202 includes a single sheet or three or more sheets.

The electrolyte can be any suitable electrolyte for an electrolytic capacitor, such as an ethylene-glycol base combined with polyphosphates, ammonium pentaborate, and/or an adipic acid solute.

Illustrated is an anode stack 203A, 203B, ..., 203N, but in various embodiments, anode stack 203A, 203B, ..., 203N includes one, two, three or more anodes having a variety of anode shapes. Each anode has a major surface 151 and an edge face 150 generally perpendicular to major surface 151. Anodes 203A, 203B, ..., 203N are generally foil structures and can include aluminum, tantalum, hafnium, niobium, titanium, zirconium, and combinations of these metals.

Figure 6:
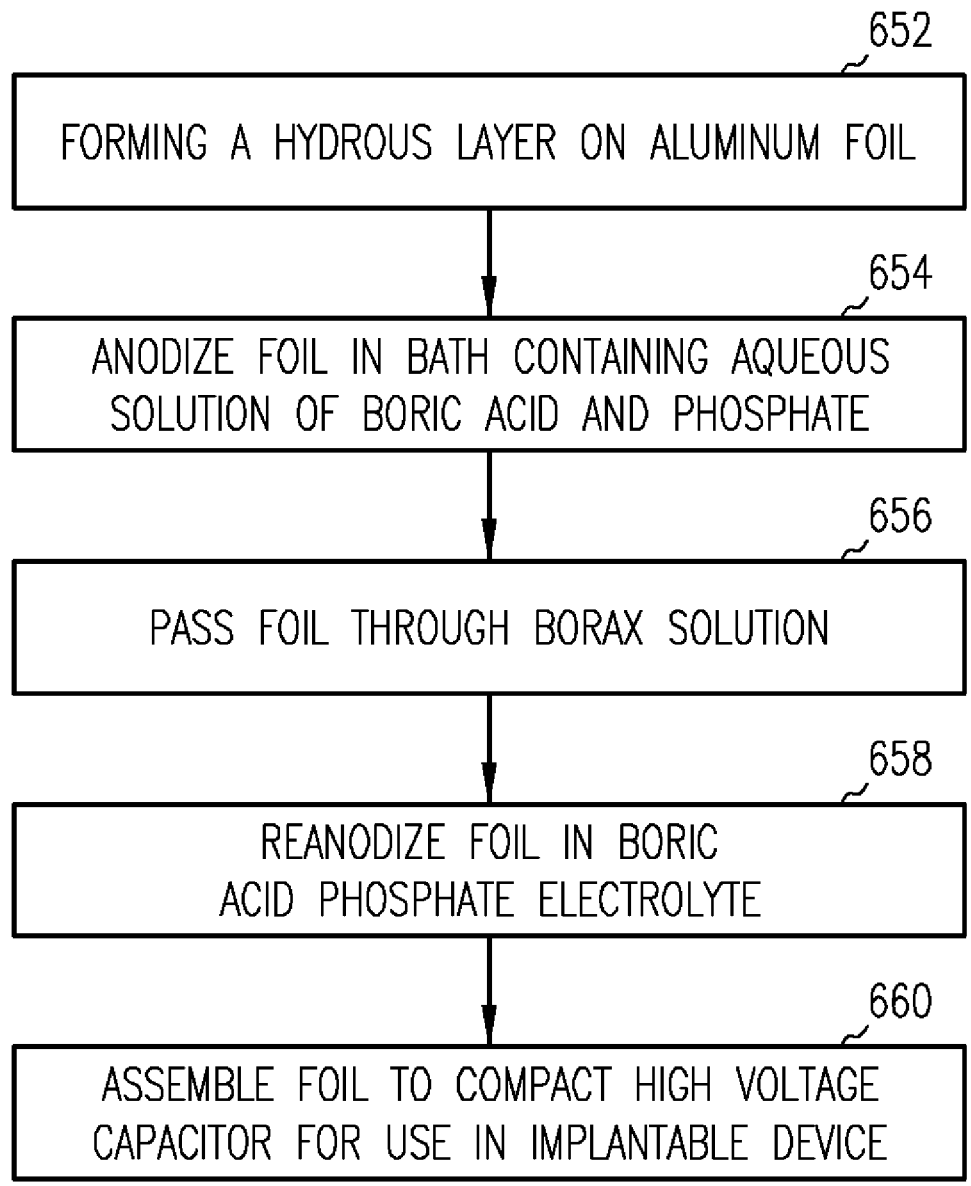
FIG. 6 illustrates an example process for the anodization of aluminum electrolytic capacitor foil, according to the present subject matter.

In one embodiment, anode foils 203A, 203B, ..., 203C are high formation voltage anode foils, examples of which are discussed in this application, including the discussion associated with example FIG. 6. In various embodiments, the anode foils are medium and/or low formation voltage foils. In one embodiment, the major surface of each anode foil 203A, 203B, ..., 203N is roughened or etched to increase its microscopic surface area. This increases the microscopic surface area of the foil with no increase in volume. Various embodiments use tunnel-etched, core-etched, and/or perforated-core-etched foil structures. Various embodiments utilize other foil compositions and classes of foil compositions.

Depending on which process is used to construct the anode, various surfaces are coated with a dielectric. For example, in embodiments where the anode shapes are punched from a larger sheet which has previously been coated with dielectric, only the surfaces which have not been sheared in the punching process are coated with dielectric. But if the dielectric is formed after punching, in various embodiments, all surfaces are coated. In some embodiments, anodes are punched from a larger sheet to minimize handling defects due to handling during the manufacturing process. For example, if a larger sheet is used as a starting material from which a number of anode layers are punched, machines or operators can grasp areas of the starting material which is not intended to form the final anode. Generally, in embodiments where the entire anode is not covered with dielectric, the anode is aged to restore the dielectric.

Various embodiments of the present subject matter include anode foils, or layers, which are only partially etched. For example, the example anodes illustrated include an substantially unetched portion 110A, 110B, ..., 110N, and an etched portion 108A, 108B, ..., 108N. In various embodiments, the etched portion 108A, 108B, ..., 108N and the unetched portion are separated by an etch gradient 109A, 109B, ..., 109N. In various embodiments, the etch gradient is structured to reduce bending stress at the etch gradient 109. Anode 203A, 203B, ..., 203N includes an etch gradient structure as described on or around pages 32-34, 115-119 of Provisional U.S. Patent Application Ser. No. 60/588,905. The teachings of those pages are incorporated herein by reference, but not by way of limitation.

In various embodiments, the present subject matter includes anodes 203A, 203B, ..., 203N, which have unetched portions 110A, 110B, ..., 110N on a single side of an anode layer. In some embodiments, these single-sided portions are substantially constrained to a single approximately planar face 151 of an anode. Additionally, single sided portions in some embodiments are primarily constrained to a first approximately planar face 151 of an anode, with sections of the unetched portion extending to second approximately planar face of the anode. In various embodiments, a second approximately planar face includes edge 150.

Figure 3:
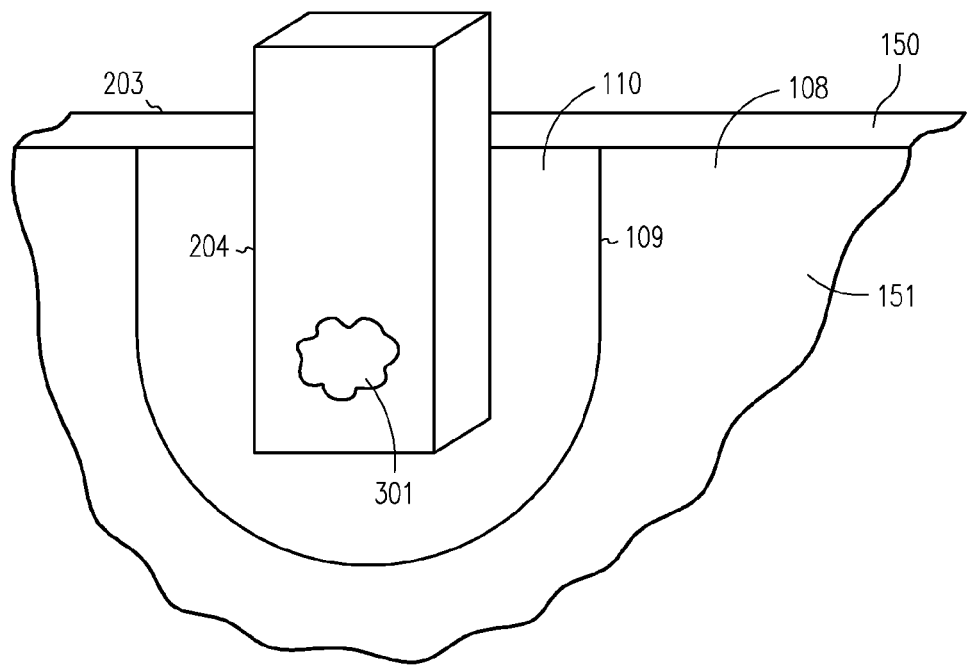
FIG. 3 is a perspective view of a connection member connected to a capacitor layer, according to one embodiment of the present subject matter.

FIG. 3 is a partial perspective view of a connection member connected to a capacitor layer, according to one embodiment of the present subject matter. In various embodiments, anode layer includes an etched portion 108, and an unetched portion 110. In various embodiment, the etched portion and the unetched portion are separated by an etch gradient 109. The etch gradient 109 can be sudden, assuming a line-shaped appearance. Additionally, etch gradient may define a gradual change, including a half-tone of varying percentages of etch. Although the unetched portion 110 is defined as semi-circular in the example illustration, other shapes are within the scope of the present subject matter. Additionally, in some embodiments, an unetched portion 110 is constrained to major surface 151, and in additional embodiments, extends to edge face 150. In some embodiments, etch gradient 109 is constrained to a major surface 151.

In various embodiments, a connection member 204 is connected to the unetched portion of the anode 203. In various embodiments, the connection between the connection member 204 and the anode 203 is solid-state. Solid state welds are known in the art. In some embodiments, the connection includes at least one joint 301 formed by a cold welding or staking process. In one embodiment, the joining process uses a small staking point. For example, in one embodiment, each joint 301 is a micro-stake joint approximately 0.015" (0.381 mm) in diameter. In other embodiments, joint 301 is less than or equal to approximately 0.030" (0.762 mm) in diameter. In some embodiments, joint 301 can range from approximately 0.005" (0.127 mm) to approximately 0.030" (0.762 mm). In some embodiments, joint 301 can range from approximately 0.010" (0.254 mm) to approximately 0.020" (0.508 mm). In various embodiments, joint 301 is a single weld, and in additional embodiments, joint 301 included multiple welds. For example, one type of multiple weld uses two stakes concurrently, on different areas of connection member 204. The following commonly assigned Provisional U.S. Patent Application, "Method and Apparatus for Single High Voltage Aluminum Capacitor Design," Ser. No. 60/588,905, filed on Jul. 16, 2004, includes additional examples of solid state connections at or around pages 16-23, 38, the examples incorporated herein by reference, but not by way of limitation.

Figure 4:
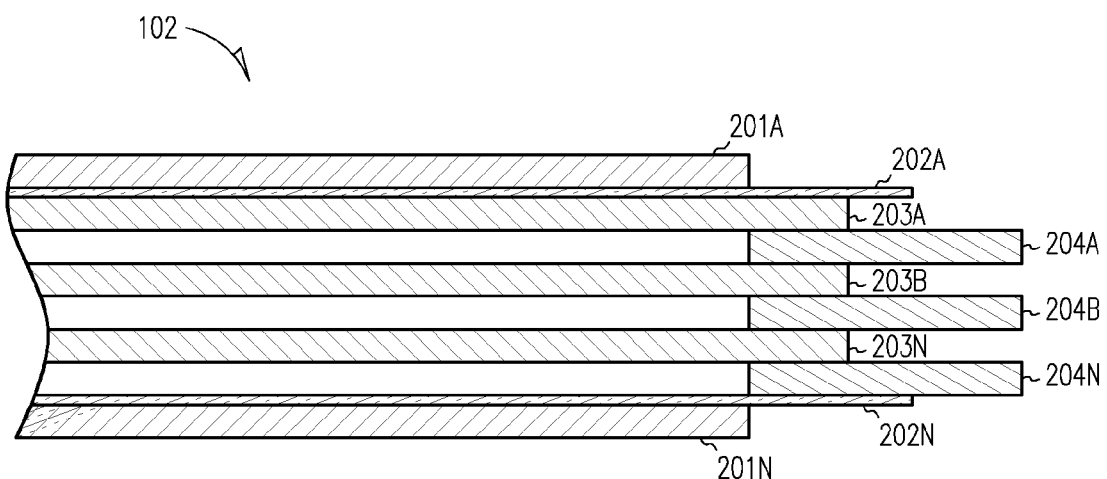
FIG. 4 is a partial side view of a capacitor stack, according to one embodiment of the present subject matter.

FIG. 4 is a side view of a partial capacitor stack, according to one embodiment of the present subject matter. In various embodiments, the view shows a cathode layers 201A, ..., 201N, separator layers 202A, ..., 202N, anode layers 203A, 203B, ..., 203N, and connection members 204A, 204B, ..., 204N. The illustration includes one configuration having 2 cathodes, 2 separator layers, three anodes, and three connection members, but other numbers of components comprising capacitor stack 102 are within the scope of the present subject matter.

Figure 5:
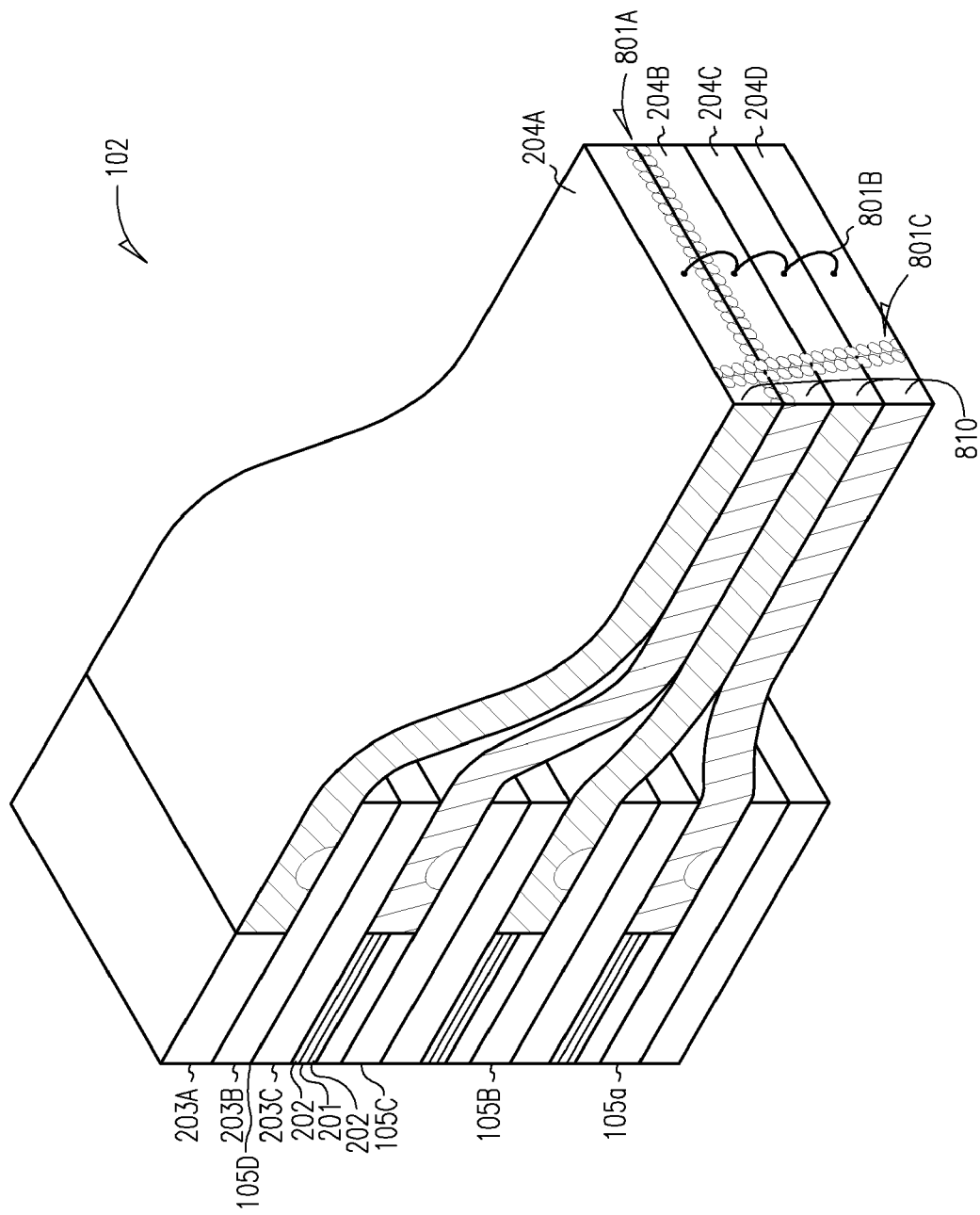
FIG. 5 is a partial cross-sectional isometric view of a capacitor having edge-connected connection members, according to one embodiment of the present subject matter.

FIG. 5 shows a connection member-to-connection member connection of a capacitor stack 102, according to one embodiment of the present subject matter. In the partial view shown, each capacitor element 105A-105D has a respective tab or connection member 204A-204D attached to it by an attachment method. In one embodiment, micro-staking is used to connect the connection members. In one embodiment, each connection member 204A-204D is approximately 0.004" (0.1016 mm) thick to fill the notch of anode foil 203A, which is 0.004" (0.1016 mm) thick. In other embodiments, the anode foil and the cathode and paper assembly have different thicknesses and so does the connection member.

Each connection member 204A-204D is positioned so that an exposed front edge face 810 of each connection member is proximal with an exposed front edge face of its neighboring connection members, forming a connection surface, such as an anode connection surface. In some embodiments, the edge faces 810 are cut to be flush with each other.

In various embodiments, each connection member 204A-204D is connected to its neighboring connection members along their respective front faces 810. This connection is a conductive interconnect. A conductive interconnect can include melted base material, as well as melted filler material, and can include a secondary structure, such as a metal bar, which is welded to each individual layer. Three embodiments of edge connections 801 are shown. Connections 801 include a laser seam edge-weld 801A, a wire bonded connection 801B, and a laser cross-wise edge-weld 801C. However, other joining processes are used. For example, in one embodiment, edge connection 801 is provided by an ultrasonic edge weld. Additionally, in various embodiments, an interconnection member, such as a ribbon of aluminum, is disposed along the front edge face 810 and connected to the front edge face 810.

In one embodiment, laser edge-weld 801A is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. In the present process, the connection members are held together in a vice, and the laser beam diameter is approximately 0.011" (0.279 mm). The laser beam is applied along the edge of connection members 204A-204D in a longitudinal manner incrementing to the left or to the right. Alternatively, other welding patterns are used to edge-weld connection members 204A-204D. In some embodiments, the connection members are welded along the horizontal axis, perpendicular to the edges of the connection members 204A-204D. (As shown in cross-wise edge-weld 801C).

In varying embodiments, edge-connecting connection members 204A, 204B, 204C, and 204D to each other provides a better electrical connection than crimping them together. Moreover, edge-connection 801, in various embodiments, creates a planar surface for attachment of a feedthrough terminal. One example of a feedthrough terminal includes a planar attachment surface. Additional examples include a ribbon connection member. The surface for connection improves manufacturing by reducing the difficulty of attaching a terminal to a plurality of anodes.

FIG. 6 illustrates an example process for the anodization of aluminum electrolytic capacitor foil, according to the present subject matter. In varying embodiments, the present subject matter is capable of producing anodized aluminum electrolytic capacitor foil at a formation voltage from about 200 volts to about 760 volts, which can result in a capacitor with a working voltage from about 150 volts to about 570 volts. For example, the present subject matter encompasses aluminum oxide formed at between approximately 600 volts and approximately 760 volts. Additionally, the present subject matter encompasses embodiments where anodization occurs from about 653 volts to about 720 volts. Additionally, the present subject matter encompasses embodiments wherein anodization occurs from about 667 volts to about 707 volts during formation.

Varied processes can be utilized to produce the aluminum foil of the present subject matter. For example, one process includes forming a hydrous oxide layer on an aluminum foil by immersing the foil in boiling deionized water 652. The aluminum foil is also subjected to electrochemical anodization in a bath containing an anodizing electrolyte 654 composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution 656. Borax, in various embodiments, includes a hydrated sodium borate, $Na_2B_4O_7 \cdot 10H_2O$, and is an ore of boron.

In varying embodiments, the foil is reanodized in the boric acid-phosphate electrolyte previously discussed 658. In various embodiments of the present subject matter, the process produces a stabilized foil suitable for oxide formation of up to approximately 760 volts.

In various embodiments, the anodizing electrolyte used in block 654 and 656 contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a the barrier layer oxide of lower quality, and foil corrosion.

Various aspects of the present subject matter include performance properties which enable the capacitor to function as a single capacitor in an implantable cardioverter defibrillator 660. For example, by constructing the capacitor stack with the methods and apparatus contained in these teachings, one may construct a capacitor which is suited for use as the sole capacitor used for powering therapeutic pulses in an implantable cardioverter defibrillator. By using a single capacitor, instead of two capacitors which are connected in series, the present subject matter contributes to weight and size reductions.

Figure 7:
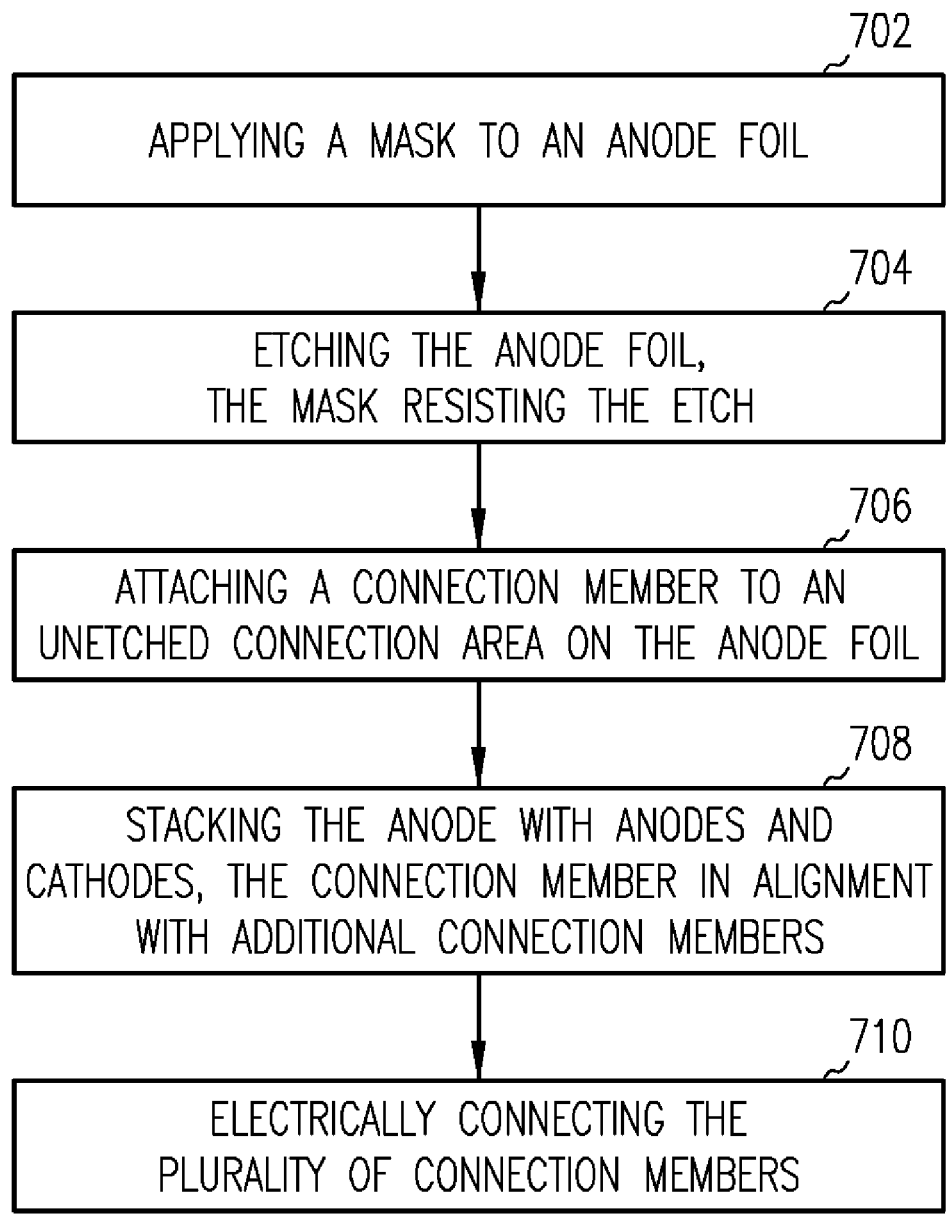
FIG. 7 illustrates a block diagram of one process for forming an anode with a connection member, according to one embodiment of the present subject matter.

FIG. 7 illustrates a block diagram of one method of making at least one partially etched anode, according to various embodiments of the present subject matter. The present subject matter includes applying a mask to an anode foil, 702. In various embodiments, applying a mask to an anode foil includes application of a mask as is discussed on or around pages 32-34 of related Provisional U.S. Patent Application "Method and Apparatus for High Voltage Aluminum Capacitor Design," Ser. No. 60/588,905, filed on Jul. 16, 2004, incorporated herein by reference, but not by way of limitation.

Various additional embodiments include etching the anode 704. Etching the anode increases the surface roughness. In one example, the present subject matter includes an unetched connection area formed by the process of applying a mask to an anode foil, etching the anode foil, and removing the mask. In one embodiment, the mask is formed by curing a resin on an anode.

In various embodiments, the present subject matter includes attaching a connection member to an unetched connection area on the anode foil 706. The present subject matter additionally includes stacking the anode with anodes and cathodes, the connection member in alignment with additional connection members 708.

In a first example, the present subject matter includes attaching a first connection member to an unetched connection area on a single side of a first anode layer. The example includes forming a capacitor stack by aligning the first anode layer with at least a second anode layer, the second anode layer having at least a second connection member, the first connection member and the second connection member for electrical connection of the anode layer to the plurality of capacitor electrodes, and aligning the first connection member and the second connection member to define an anode connection surface.

In a second example, the present subject matter includes forming a capacitor stack by assembling the first anode layer with at least one cathode layer, the assembled first anode layer and at least one cathode layer defining an element, and stacking at least two elements in alignment.

In a third example, the present subject matter includes forming a capacitor stack by positioning the first connection member and the second connection member so that the first connection member and the second connection member are separated by a distance, the distance approximately equal to the thickness of the second anode layer. Additionally, the third examples includes aligning the first connection member and the second member by bending them together, putting the first connection member and the second connection member into adjacent positions.

In these examples, as well as in additional embodiments not enumerated here, a connection member is more malleable than is an etched surface such as an etched anode surface. By including a connection member which has improved malleability, various processes can deform the connection members into forming an aligned connection surface without damaging structure. Damaged structure, in embodiments without malleable structures, includes cracked sections of anodes which do not deform as elastically under bending stress as is needed for a process.

In additional embodiments, the present subject matter includes electrically connecting the plurality of connection members 710. This can include connections using welds with or without filler metal. This can also include connections using an additional structure, such as a bar welded to the connection members. In various embodiments, one example includes connecting an anode interconnect to the anode connection surface. An anode connection surface, in various embodiments, is formed by aligning two or more edges, such as connection member edges, adjacently, so that the edges are positioned proximal. The example FIG. 5 demonstrates a surface 810 which can serve as one example of an anode connection surface.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

What is claimed is:

1. A method, comprising:
   joining a first connection member to an unetched connection area, the unetched connection area located on a single major surface of a first planar anode;
   forming a capacitor stack by aligning the first planar anode with at least a second planar anode, the second planar anode including at least a second connection member, the first connection member and the second connection member for electrical connection of the first planar anode to the second planar anode;
   filling a space defined by the first planar anode, the first connection member, and a further anode layer stacked onto the first planar anode and the first connection member by stacking into the space a first separator, a cathode and a second separator into the space;
   aligning the first connection member and the second connection member to define an anode connection surface; and
   joining the first planar anode and the second planar anode.

2. The method of claim 1, further comprising:
   assembling the first planar anode with at least one planar cathode, the assembled first planar anode and the at least one planar cathode defining an element,
   wherein stacking includes stacking the element into the capacitor stack.

3. The method of claim 1, further comprising:
   bending the first connection member and the second connection member such that the first connection member and the second connection member define the anode connection surface.

4. The method of claim 1, wherein joining the first planar anode and the second planar anode includes welding the first connection member to the second connection member to electrically connect the first connection member to the second connection member.

5. The method of claim 4, wherein welding includes solid-state welding.

6. The method of claim 4, wherein welding includes laser welding.

7. The method of claim 1, further comprising:
positioning an interconnection member against the anode connection surface; and
welding together the first connection member, the second connection member and the interconnection member.

8. The method of claim 1, further comprising:
applying a mask to an anode foil;
etching the anode foil; and
removing the mask.

9. The method of claim 8, wherein applying a mask includes curing a resin to the first planar anode.

10. The method of claim 8, wherein applying the mask onto the anode foil includes defining a gradient between a masked portion and an unetched portion, the gradient crossing a transition line a plurality of times.

11. The method of claim 1, wherein joining the first planar anode and the second planar anode includes joining the first planar anode and the second planar anode with an interconnection member.

12. The method of claim 11, wherein joining the first planar anode and the second planar anode includes joining the first planar anode and the second planar anode with an interconnection member disposed on the connection surface.

13. The method of claim 11, wherein the unetched connection area of the first planar anode layer is formed by the process comprising:
applying a mask to an anode foil, etching the anode foil; and
removing the mask.

14. The method of claim 13, wherein the mask is a resin cured to the first planar anode layer.

15. The method of claim 11 wherein forming a capacitor stack further comprises:
assembling the first planar anode layer with at least one planar cathode layer, the assembled first planar anode layer and the at least one planar cathode layer defining an element; and
stacking the first element with at least one planar anode layer.

16. The method of claim 11, wherein forming a capacitor stack further comprises positioning the first connection member and the second connection member so that the first connection member and the second connection member are separated by a distance, the distance approximately equivalent to the thickness of the second planar anode layer.

17. The method of claim 11, wherein aligning the first connection member and the second member further comprises bending the first connection member and the second connection member into an abutting position.

18. The method of claim 1, further comprising:
defining an element by assembling the first planar anode, the first separator, the cathode, the second separator layer, the first connection member and the further anode layer; and
stacking the first element with the second planar anode.

19. The method of claim 1, further comprising roughening a surface of the first planar anode.

20. The method of claim 1, further comprising:
disposing the capacitor stack into a capacitor case;
electrically coupling the first connection member to a feedthrough disposed through the capacitor case and electrically insulated from the case;
electrically coupling the cathode to the case;
filling the case with electrolyte; and
sealing the case to retain electrolyte.

* * * * *

UNITED STATES PATENT AND TRADEMARK OFFICE
CERTIFICATE OF CORRECTION

| | | |
|---|---|---|
| PATENT NO. | : 7,846,217 B2 | Page 1 of 8 |
| APPLICATION NO. | : 12/380172 | |
| DATED | : December 7, 2010 | |
| INVENTOR(S) | : James M. Poplett | |

Figure 8:
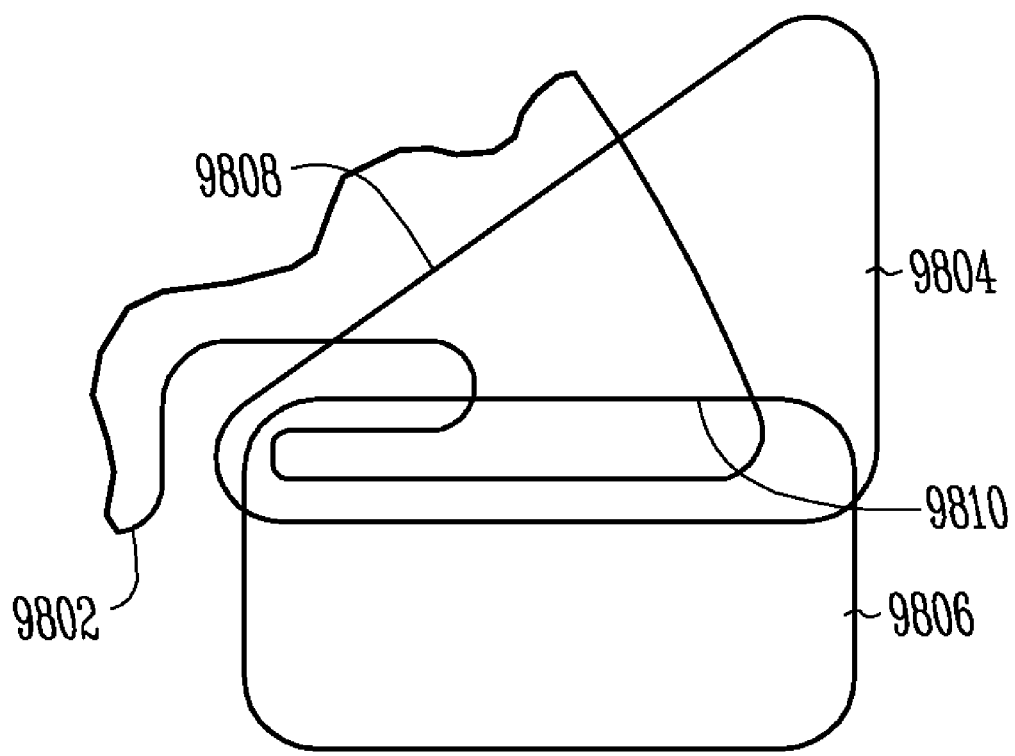
FIG. 8 illustrates one example of a mask applied to the electrode of the present subject matter. In varying embodiments, a mask is applied to one or both sides of the electrode. For example, line 9802 defines a portion of an electrode shape which is punched from a sheet, in varying embodiments of the present subject matter. Applied to the sheet are a first mask 9804 and a second mask 9806. In varying embodiments, including the embodiment pictured, masked portions eclipse the eventual shape of the electrode, represented by electrode shape 9802.

It is certified that error appears in the above-identified patent and that said Letters Patent is hereby corrected as shown below:

In columns 3-6, line 26 (Col. 3) - 3 (Col. 6), below "FIG. 7 illustrates a block diagram of one process for forming an anode with a connection member, according to one embodiment of the present subject matter," delete "FIG. 8 illustrates one example of a mask applied to the electrode of the present subject matter. In varying embodiments, a mask is applied to one or both sides of the electrode. For example, line 9802 defines a portion of an electrode shape which is punched from a sheet, in varying embodiments of the present subject matter. Applied to the sheet are a first mask 9804 and a second mask 9806. In varying embodiments, including the embodiment pictured, masked portions eclipse the eventual shape of the electrode, represented by electrode shape 9802.

For example, the sheet includes a first major surface which is visible, and a second major surface substantially parallel to the first which is hidden. In varying embodiments, a first pattern of mask 9804 is applied to the first surface, and a second pattern of mask 9806 is applied to the second surface.

In varying embodiments, the first pattern of mask 9804 and the second pattern of mask 9806 are shaped differently. In one example, the first and second pattern have different shapes, and cover varying areas of the sheet. For example, pattern 9804 covers a first area of electrode shape 9802, and pattern 9806 covers a second area of electrode shape 9802, and the first area covered by pattern 9804 of electrode shape 9802 is larger than the second area covered by pattern 9806 of electrode shape 9802.

It should be noted that in varying embodiments, the shape of pattern 9804 and the shape of pattern 9806 are chosen to assist in manufacturing. For example, in varying embodiments, electrode shape 9802 is cut from a sheet of Signed and Sealed this
Twenty-ninth Day of March, 2011

David J. Kappos
*Director of the United States Patent and Trademark Office* etched and anodized electrodes. When a single sheet is populated with multiple electrodes, in varying embodiments, the choice of shape for pattern 9804 and pattern 9806 can aid in associated manufacturing steps.

In varying embodiments, transition line 9808 is skew to transition line 9810. Varying examples increase the bending stress at the transition between etched foil and non-etched foil, and by positioning the transition line 9808 and 9810 in varying configurations, the bending stress of the electrode 9802 is more evenly distributed about the foil, which, in some embodiments, reduces instances of cracking and breaking.

FIGS. 9A-9F illustrate varying patterns of mask for application to a foil, according to various embodiments of the present subject matter. In varying embodiments, the mask can populate the pattern 9804 or the pattern 9806 illustrated in FIG. 8. It should be noted that the line 9902 described in varying examples is equivalent to the line 9808 of pattern 9804, and line 9810 of pattern 9806.

FIG. 9A illustrates an example of a mask constructed out of a pattern of rounded square shapes arranged proximal to each other. In varying embodiments, the shapes cover approximately 80% of the surface onto which they are printed, proximal the line 9902. Line 9902 defines, and the area proximal the line, define a transition zone between masked electrode and non-masked electrode. By angling the line 9902 in relation to other lines which define the mask, the pattern includes a varied interface at line 9902. The pattern at line 9902 resembles a set of steps.

Through the angle at line 9902, the pattern reduce instances of electrode breakage proximal to the transition zone. For example, in some embodiments, the electrode is etched and exhibits undercutting at the border between a masked portion and a non-masked portion. Parallel to this border is an axis which approximately bisects the undercut. Undercutting, in varying embodiments, results in a portion of the electrode which is weak while bending along the axis which bisects the length of the undercut. However, in varying embodiments, the undercut portion of the electrode is strong when bending orthogonal to an axis bisecting the length of the undercut. Thus, undercutting increases bending stress more in certain directions. By arranging the masking patter in the manner illustrated, the undercut portions of the electrode can be controlled to improve the flexibility of the electrode which reduces instances of breaking or cracking.

FIG. 9B illustrates an example of a mask constructed out of a pattern of rounded squares arranged proximal to each other. In varying embodiments, line 9902 defines an area across which elongate shapes span. It is apparent upon reading and understanding these teachings that the elongate shapes can be constructed out of rounded blocks, and that the elongate shapes can be defined in other fashions.

In varying embodiments, the mask includes exposed area 9908. In one example, exposed area 9908 is sized such that undercutting at the exposed area 9908 during etch does not substantially weaken the electrode under bending stress.

FIG. 9C illustrates one example of a halftone suitable for strengthening an electrode at the juncture between a masked portion and an unmasked portion. In one embodiment, the half tone is comprised for smaller rounded blocks 9904, and larger rounded blocks 9906. In one embodiment, the reach of the halftone is defined by a line 9902, and is limits to a transition zone proximal to the line 9902. In additional embodiments, the halftone is not defined as such.

In varying embodiments, the halftone transitions from covering approximately 80% of the electrode at the masked transition zone, to covering approximately 60% of the electrode at the masked transition zone. In varying embodiments, this can be accomplished with rounded blocks placed proximal to each other, and in additional embodiments, it is accomplished with other shapes arranged in a predictable pattern, such as a grid, or in a random pattern.

FIG. 9D illustrates an example of a halftone suitable for strengthening an electrode at the junction between a masked portion and an unmasked portion.

FIG. 9E illustrates an example of a pattern useful for strengthening an electrode in the region of a transition from a masked area to an unmasked area, according to various embodiments of the present subject matter. By including a sinusoidal shape which spans the line 9902, the instances of undercutting which are parallel to the bending line (the bending line is approximately parallel to transition line 9902) are minimized.

FIG. 9F illustrates a pattern for strengthening an electrode in an area where undercutting is put in bending stress, according to various embodiments of the present subject matter. In varying embodiments, the pattern is comprised of elongate shapes 9910. In varying embodiments, the elongate shapes demonstrate an improved resistance to cracking and breaking when the etched foil is subjected to bending stresses which are proximal the transition line 9902.

FIG. 10 shows a process for producing a foil 9950 with a partially etched area, according to various embodiments of the present subject matter. In varying examples, the process includes depositing a curable mask onto a foil 9952. For example, in one embodiment, the mask is deposited on a foil using a computer controlled mask dispensing system. In one example, ink is deposited using an ink jet process.

The control systems shown and described here can be implemented using software, hardware, and combinations of software and hardware. As such, the term "system" is intended to encompass software implementations, hardware implementations, and software and hardware implementations.

In various embodiments, the methods provided above are implemented as a computer data signal embodied in a carrier wave or propagated signal, that represents a sequence of instructions which, when executed by a processor, cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Additional embodiments cure the mask onto the foil 9954. Examples of curable mask include ink, and photoresist. In varying embodiments, the curable mask is cured to the foil. For example, in one embodiment, ink is deposited on the foil, and then is baked to the foil in an oven. Baking, in some embodiments, exposes the curable mask to radiant heat energy, which can increase hardness or the curable mask, and which also can decrease the time needed for curing. In varying embodiments, the oven is adapted to cure the curable mask without affecting the foil otherwise.

In varying embodiments, the foil is etched 9956, and the mask protects the foil from the etchant. Etching, in varying embodiments, is described in the discussion associated with FIG. 10, but in other embodiments, variations of the etching process are used.

Varying examples of the process then remove the mask 9958. Removing the mask, in one embodiment, includes submerging the foil with mask in a solution adapted to dissolve the mask.

Some embodiments anodize the foil 9960. Anodization, in one embodiment, is accomplished by the process discussed in the teachings associated with FIG. 10. However, these teachings should not be understood to be exhaustive or exclusive, and other methods of forming a dielectric on a foil are within the scope of the present subject matter. Additionally, it should be noted that other examples anodize the foil while the mask is in place.

CERTIFICATE OF CORRECTION (continued)
U.S. Pat. No. 7,846,217 B2

Varying embodiments cut the anodized foil into shapes 9962, and in some examples, the foil shapes are then assembled into a capacitor 9964."

In column 7, line 11, below "In various embodiments, the etch gradient is structured to reduce bending stress at the etch gradient 109. Etch gradient structure are described on or around pages 32-34, 115-119 of Provisional U.S. Patent Application Ser. No. 60/588,905. The teachings of those pages are incorporated herein by reference, but not by way of limitation," and insert -- FIG. 8 illustrates one example of a mask applied to the electrode of the present subject matter. In varying embodiments, a mask is applied to one or both sides of the electrode. For example, line 9802 defines a portion of an electrode shape which is punched from a sheet, in varying embodiments of the present subject matter. Applied to the sheet are a first mask 9804 and a second mask 9806. In varying embodiments, including the embodiment pictured, masked portions eclipse the eventual shape of the electrode, represented by electrode shape 9802.

For example, the sheet includes a first major surface which is visible, and a second major surface substantially parallel to the first which is hidden. In varying embodiments, a first pattern of mask 9804 is applied to the first surface, and a second pattern of mask 9806 is applied to the second surface.

In varying embodiments, the first pattern of mask 9804 and the second pattern of mask 9806 are shaped differently. In one example, the first and second pattern have different shapes, and cover varying areas of the sheet. For example, pattern 9804 covers a first area of electrode shape 9802, and pattern 9806 covers a second area of electrode shape 9802, and the first area covered by pattern 9804 of electrode shape 9802 is larger than the second area covered by pattern 9806 of electrode shape 9802.

It should be noted that in varying embodiments, the shape of pattern 9804 and the shape of pattern 9806 are chosen to assist in manufacturing. For example, in varying embodiments, electrode shape 9802 is cut from a sheet of etched and anodized electrodes. When a single sheet is populated with multiple electrodes, in varying embodiments, the choice of shape for pattern 9804 and pattern 9806 can aid in associated manufacturing steps.

In varying embodiments, transition line 9808 is skew to transition line 9810. Varying examples increase the bending stress at the transition between etched foil and non-etched foil, and by positioning the transition line 9808 and 9810 in varying configurations, the bending stress of the electrode 9802 is more evenly distributed about the foil, which, in some embodiments, reduces instances of cracking and breaking.

FIGS. 9A-9F illustrate varying patterns of mask for application to a foil, according to various embodiments of the present subject matter. In varying embodiments, the mask can populate the pattern 9804 or the pattern 9806 illustrated in FIG. 8. It should be noted that the line 9902 described in varying examples is equivalent to the line 9808 of pattern 9804, and line 9810 of pattern 9806.

FIG. 9A illustrates an example of a mask constructed out of a pattern of rounded square shapes arranged proximal to each other. In varying embodiments, the shapes cover approximately 80% of the surface onto which they are printed, proximal the line 9902. Line 9902 defines, and the area proximal the line, define a transition zone between masked electrode and non-masked electrode. By angling the line 9902 in relation to other lines which define the mask, the pattern includes a varied interface at line 9902. The pattern at line 9902 resembles a set of steps.

Through the angle at line 9902, the pattern reduce instances of electrode breakage proximal to the transition zone. For example, in some embodiments, the electrode is etched and exhibits undercutting at the border between a masked portion and a non-masked portion. Parallel to this border is an axis which approximately bisects the undercut. Undercutting, in varying embodiments, results in a portion of the electrode which is weak while bending along the axis which bisects the length of the undercut. However, in varying embodiments, the undercut portion of the electrode is strong when bending orthogonal to an axis bisecting the length of the undercut. Thus, undercutting increases bending stress more in certain directions. By arranging the masking patter in the manner illustrated, the undercut portions of the electrode can be controlled to improve the flexibility of the electrode which reduces instances of breaking or cracking.

FIG. 9B illustrates an example of a mask constructed out of a pattern of rounded squares arranged proximal to each other. In varying embodiments, line 9902 defines an area across which elongate shapes span. It is apparent upon reading and understanding these teachings that the elongate shapes can be constructed out of rounded blocks, and that the elongate shapes can be defined in other fashions.

In varying embodiments, the mask includes exposed area 9908. In one example, exposed area 9908 is sized such that undercutting at the exposed area 9908 during etch does not substantially weaken the electrode under bending stress.

FIG. 9C illustrates one example of a halftone suitable for strengthening an electrode at the juncture between a masked portion and an unmasked portion. In one embodiment, the half tone is comprised for smaller rounded blocks 9904, and larger rounded blocks 9906. In one embodiment, the reach of the halftone is defined by a line 9902, and is limits to a transition zone proximal to the line 9902. In additional embodiments, the halftone is not defined as such.

In varying embodiments, the halftone transitions from covering approximately 80% of the electrode at the masked transition zone, to covering approximately 60% of the electrode at the masked transition zone. In varying embodiments, this can be accomplished with rounded blocks placed proximal to each other, and in additional embodiments, it is accomplished with other shapes arranged in a predictable pattern, such as a grid, or in a random pattern.

FIG. 9D illustrates an example of a halftone suitable for strengthening an electrode at the junction between a masked portion and an unmasked portion.

FIG. 9E illustrates an example of a pattern useful for strengthening an electrode in the region of a transition from a masked area to an unmasked area, according to various embodiments of the present subject matter. By including a sinusoidal shape which spans the line 9902, the instances of undercutting which are parallel to the bending line (the bending line is approximately parallel to transition line 9902) are minimized.

FIG. 9F illustrates a pattern for strengthening an electrode in an area where undercutting is put in bending stress, according to various embodiments of the present subject matter. In varying embodiments, the pattern is comprised of elongate shapes 9910. In varying embodiments, the elongate shapes demonstrate an improved resistance to cracking and breaking when the etched foil is subjected to bending stresses which are proximal the transition line 9902.

FIG. 10 shows a process for producing a foil 9950 with a partially etched area, according to various embodiments of the present subject matter. In varying examples, the process includes depositing a curable mask onto a foil 9952. For example, in one embodiment, the mask is deposited on a foil using a computer controlled mask dispensing system. In one example, ink is deposited using an ink-jet process.

The control systems shown and described here can be implemented using software, hardware, and combinations of software and hardware. As such, the term "system" is intended to encompass software implementations, hardware implementations, and software and hardware implementations.

In various embodiments, the methods provided above are implemented as a computer data signal embodied in a carrier wave or propagated signal, that represents a sequence of instructions which, when executed by a processor, cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Additional embodiments cure the mask onto the foil 9954. Examples of curable mask include ink, and photoresist. In varying embodiments, the curable mask is cured to the foil. For example, in one embodiment, ink is deposited on the foil, and then is baked to the foil in an oven. Baking, in some embodiments, exposes the curable mask to radiant heat energy, which can increase hardness or the curable mask, and which also can decrease the time needed for curing. In varying embodiments, the oven is adapted to cure the curable mask without affecting the foil otherwise.

In varying embodiments, the foil is etched 9956, and the mask protects the foil from the etchant. Etching, in varying embodiments, is described in the discussion associated with FIG. 10, but in other embodiments, variations of the etching process are used.

Varying examples of the process then remove the mask 9958. Removing the mask, in one embodiment, includes submerging the foil with mask in a solution adapted to dissolve the mask.

Some embodiments anodize the foil 9960. Anodization, in one embodiment, is accomplished by the process discussed in the teachings associated with FIG. 10. However, these teachings should not be understood to be exhaustive or exclusive, and other methods of forming a dielectric on a foil are within the scope of the present subject matter. Additionally, it should be noted that other examples anodize the foil while the mask is in place.

Varying embodiments cut the anodized foil into shapes 9962, and in some examples, the foil shapes are then assembled into a capacitor 9964. --